United States Patent [19]
Bauman et al.

[11] Patent Number: 5,154,716
[45] Date of Patent: Oct. 13, 1992

[54] BOTTOM BLOOD BAG SEPARATION SYSTEM

[75] Inventors: Ronald H. Bauman, Arcadia; Donald R. Denton, San Dimas; William W. Dupin, Covina; Edward J. Nelson, San Rafael; Eva Sajan, Oakland, all of Calif.

[73] Assignee: Miles Inc., Elkhart, Ind.

[21] Appl. No.: 609,498

[22] Filed: Nov. 6, 1990

[51] Int. Cl.$^5$ .............................................. B01D 37/00
[52] U.S. Cl. ........................................ 604/410; 604/4; 604/5; 604/6; 210/767; 210/782
[58] Field of Search ...................................... 604/4-6, 604/410, 406, 409, 408, 411; 210/206

[56] References Cited

U.S. PATENT DOCUMENTS

| | | | |
|---|---|---|---|
| 3,304,977 | 1/1965 | Hammons | 150/1 |
| 3,911,918 | 10/1975 | Turner | 128/272 |
| 4,146,172 | 3/1979 | Cullis et al. | 604/410 X |
| 4,316,576 | 2/1982 | Cullis et al. | 604/6 |
| 4,413,771 | 11/1983 | Rohde et al. | 604/410 |
| 4,435,179 | 3/1984 | Walker | 604/410 |
| 4,617,009 | 10/1986 | Ohlin et al. | 604/410 |
| 4,720,284 | 1/1988 | McCarty | 604/410 |
| 4,997,577 | 3/1991 | Stewart | 604/410 |

Primary Examiner—Robert A. Hafer
Assistant Examiner—Kerry Owens
Attorney, Agent, or Firm—Elizabeth F. Enayati; James A. Giblin

[57] ABSTRACT

Plastic blood bag system including a bag having a generally longitudinal seal extending from the top of the bag and between two blood bag ports downwardly to at least the lower half of the bag but not to the bottom of the bag, thereby leaving the sole passageway within the bag and between two ports located in the lower half of the bag.

10 Claims, 3 Drawing Sheets

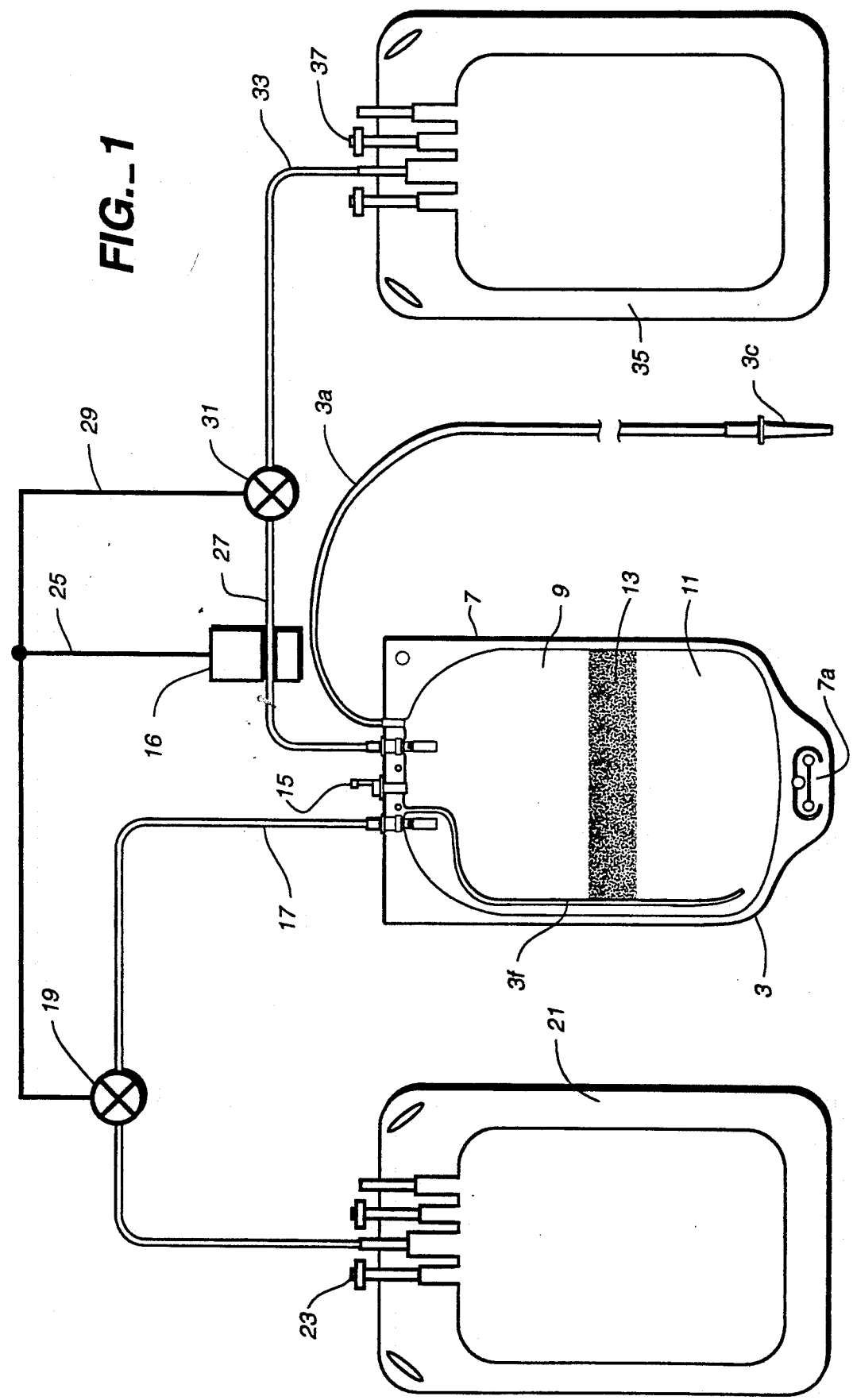
FIG._1

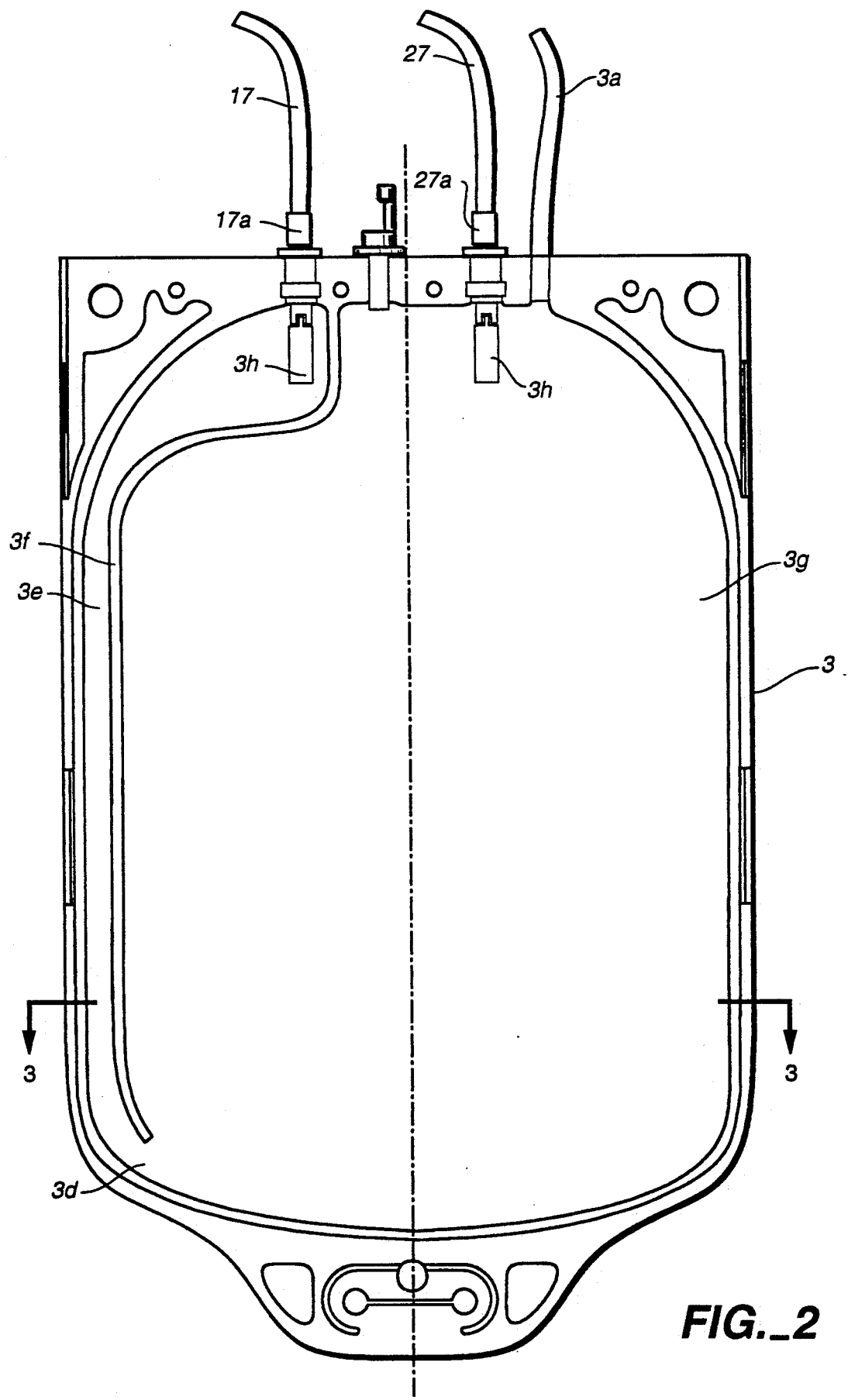
FIG._2

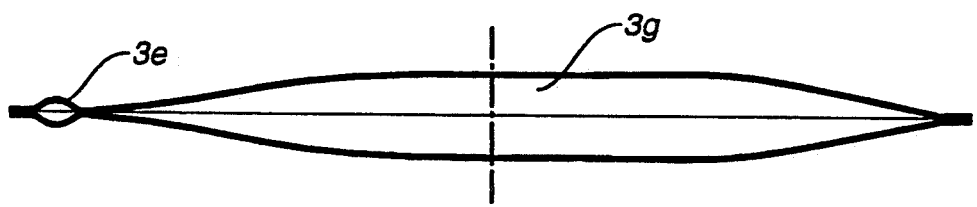
FIG._3

BOTTOM BLOOD BAG SEPARATION SYSTEM

RELATED APPLICATION

U.S. patent application Ser. No. 07/493,024 filed Mar. 13, 1990 in the names of R. A. Carmen et al and entitled, "Blood Separation System".

BACKGROUND OF THE INVENTION

1. Field

This disclosure is concerned generally with the collection and separation of whole blood into useful components and specifically with a plastic blood bag system which permits a more dense centrifuged component in the lower part of the bag to be expressed to and out of the top of the bag.

2. Prior Art

Whole blood is commonly separated into its major components of less dense plasma and more dense red blood cells (RBCs) by first drawing the whole blood into a plastic bag known as a donor or primary bag. The bag contents are then centrifuged under controlled conditions to result in a lower, more dense portion of packed RBCs and an upper less dense plasma portion, which may be rich in platelets (platelet rich plasma or PRP).

The donor bag is typically connected via blood bag ports by plastic tubing to one or more satellite bags to form a "closed" system into which separated blood components (e.g., the PRP or RBCs) may be expressed by external manipulation and valves for further processing or use.

The above system for separating blood into its major components has remained generally unchanged since the 1950's when plastic blood bags were introduced commercially on a large scale.

In recent times, efforts have focused on preparing very specific "components" from whole blood (or fractionated plasma) so that if a patient needs a certain component (e.g., coagulation factors, albumin, platelets, ISG, RBCs, etc.), only that specific component can be administered. Although the system of this disclosure may be used to prepare other blood products, it is especially useful for preparing platelets.

The classical method of preparing platelet transfusion products from whole blood consists of an initial centrifugation of whole blood in a plastic blood bag at relatively low centrifugal force to separate most of the PRP from the red cells. The PRP is then commonly expressed into an attached satellite blood bag. This is followed by centrifugation of the PRP in the satellite bag at relatively high centrifugal force. This results in a lower sediment of platelets and an upper platelet poor plasma (PPP). The sedimented platelets are in the form of a pellet or "button" which is resuspended in a small volume of the PPP donor plasma (50–60 ml) to give the platelet concentrate (PC).

With good technique, about ⅔ of the platelets in a whole blood collection unit (about 450 ml±10%) are recovered in the platelet concentrate. This is equivalent to about $8 \times 10^{10}$ platelets per concentrate. However, achieving this yield of platelets requires strict attention to centrifugation protocols, frequent calibration of the centrifuges, and operator diligence. The fact that the minimum standard for platelet yield is only $5.5 \times 10^{10}$ per concentrate attests to the operator-dependent nature of this procedure.

Recently, some transfusion services in Europe have begun to investigate and in some cases employ an alternate method of platelet preparation, specifically preparation from the "buffy coat" of centrifuged whole blood. In this procedure the initial centrifugation of whole blood is performed at relatively high centrifugal force to form three portions: an upper layer of relatively cell-free plasma, an intermediate "buffy coat" layer containing platelets and leukocytes, and a lower layer of red cells.

The intermediate buffy coat is separated and mixed with either a small volume of plasma (50–60 ml) or a synthetic medium. The mixture is then centrifuged at low centrifugal force to separate platelet concentrate (upper layer) from leukocytes (WBCs) and residual red cells. Data suggest that platelets prepared in this fashion are of improved quality, presumably because platelet activation that would otherwise occur during the pelleting step of the PRP centrifugation method is avoided.

The original work on buffy coat platelets was done at the Dutch Red Cross. Referred to as the Amsterdam method, it employed a standard quadruple multiple plastic bag system. After centrifugation of blood and removal of plasma from the main bag, the buffy coat layer was transferred to an empty connected satellite bag and then processed to platelet concentrate. Using this method, Pietersz et al (Vox Sang 1985; 49:81–85) found a mean of $7.2 \times 10^{10}$ platelets per concentrate; the volume of blood collected in this study was about 500 Ml. Kretschmer et al (Infusionstherapie 1988; 15:232-239) found a mean of $6.3 \times 10^{10}$ platelets per concentrate from 450 ml blood collections.

The Amsterdam method, while apparently giving respectable platelet yields, was cumbersome and labor-intensive. The buffy coat transfer step required the operator to massage the bag to prevent hang-up of the "sticky" buffy coat layer. These manipulations might influence platelet function and release of granulocyte enzymes. There was also no way to control the volume of buffy coat removed.

Other efforts to improve blood separation procedures or at least make it less burdensome are known. For example, U.S. Pat. No. 3,911,918 to Turner discloses a blood bag having an hour glass shape. That bag has a top portion for plasma, a bottom portion for RBCs and a middle portion for platelets and white blood cells. The hour glass shape is said to help position clamping or sealing devices at the juncture of the separated components after whole blood in the bag is centrifuged. This system has not been used on any significant commercial scale to date. See also U.S. Pat. No. 4,857,190 to S. Wada and B. Kuhlemann showing a blood bag having a continuous but smaller receptacle adapted to help collect and define the interface of a centrifuged component.

In U.S. Pat. No. 4,608,178 to A. S. Johansson and C. F. Hogman there is disclosed a "top/bottom" bag in which the upper and lower portions of separated blood components can be simultaneously expressed from a specially designed bag which leaves behind in the bag the intermediate portion known as buffy coat. The expression of that system is controlled by a pressure plate on the bag and sensors which monitor the position of the intermediate layer such that it remains in the bag while the upper plasma is expressed from a top part and the lower red blood cells are expressed from a bottom part in the bag. Hence, the name top/bottom bag. The sensors in that system assure the simultaneous expression of the top and bottom components.

The above described systems are fairly recent and it is not clear yet whether those systems will in time replace existing blood separation systems based on the use of a relatively simple unmodified donor bag.

However, the systems do offer new ways to separate WBCs from platelets or to prepare platelets (contained in the intermediate or buffy coat portion). The patent to Johansson and Hogman show how to do this in a semi-automated manner. Hence, it potentially represents a semi-automated way to prepare platelets.

In an effort to overcome problems associated with the Amsterdam method, Johansson and Hogman (see above-cited patent) developed the bag system with the top and bottom drainage of the primary bag and a sensor device which allowed partially automated blood separation. Kretschmer et al, cited above, used that type of system to prepare platelet concentrates from buffy coats and found a mean of $6.7 \times 10^{10}$ platelets per unit.

In co-pending patent application Ser. No. 07/493,024 filed in the names of R. A. Carmen et al, there is disclosed another system for removing the lower contents of a blood bag in a relatively simple way. That system uses a tubular member which extends from an upper port into the interior of the bag, terminating just above the bag bottom. When pressure is applied to the bag, the lower contents of the bag exit through the tubular member and the top of the bag.

Although the above system has been found useful and may be a practical alternative to the top-bottom bag, we have now found what may be an even more practical alternative which uses a novel blood bag construction that offers surprising manufacturing and use advantages. Details of the system are described below.

SUMMARY OF INVENTION

Our blood separation system comprises a main plastic blood bag (a primary bag or a donor bag) in which separated components can be expressed from the top of the bag and in an order chosen by the operator.

The system includes a main or donor bag having a generally longitudinal seal extending from the top of the bag and between two blood bag ports downwardly to at least the lower half of the bag but not to the bottom of the bag, thereby leaving an internal passageway between the two ports that is located in the lower half of the bag.

In one use, whole blood (or a component to be separated) is introduced into the bag through one port via conventional methods. The whole blood is then centrifuged to form a lighter portion and a more dense portion. If desired, the denser portion can then be removed from the lower part of the bag before removal of the upper less dense component by applying pressure (which can be manual or automated) to the bag to push substantially all of the denser component through the internal passageway to one side of the longitudinal seal and out of the bag through the port communicating with that side of the longitudinal seal. That port must, of course, be opened for fluid flow.

In preferred embodiments, the longitudinal seal is relatively narrow (e.g. <5 mm wide), generally parallel and close to one side edge of the bag, and terminates at its lower portion within the lower 50% (preferably within the lower 10%) of the bag length. In very preferred embodiments, the volume of the side through which the more dense component exits the bag is less than 10% of the total bag volume. The system may be used with electronic monitoring means (see below) to provide semi-automated blood separation.

BRIEF DESCRIPTION OF THE FIGURES

FIG. 1 is a plan view of one preferred blood bag separation system.

FIG. 2 is a plan view of a plastic bag illustrating one embodiment of the main bag of the invention.

FIG. 3 is a cross sectional view of the bag in FIG. 1 taken through lines 2—2 of FIG. 2.

SPECIFIC EMBODIMENTS

Our preferred system for the separation of blood components comprises a main donor bag having optical sensor-activated clamps or valves associated with conventional tubings communicating with each of the outlet ports of the bag. The outlet port for the more dense component communicates with the internal passageway toward the bottom of the bag interior. In preferred embodiments, the longitudinal seal is, on average, within about 7 mm of the edge seal at one side of the bag (in a flattened, empty bag). The longitudinal seal also preferably extends to within about 7 mm of the seal at the interior bottom of the bag. Preferably, the bag is made using simple, conventional seals for the top, bottom, side and longitudinal seals. When the bag is filled with fluid (and balloons out), the resulting passageway toward the bag bottom will have an average diameter of less than about 7 mm.

One preferred system is a "triple" blood bag consisting of a primary or donor bag and two satellite bags pre-connected to the primary bag by conventional PVC blood bag tubing and fittings. The bags themselves may be made from conventional PVC plastic film used to make blood bags (e.g., PVC plasticized with plasticizer such as DEHP, TOTM, citrate esters and the like) or from other acceptable plastic materials (e.g. polyolefins). The primary bag is made using conventional techniques but is modified in that the blood collection bag has the longitudinal seal extending from between two top ports toward the bottom of the bag as shown generally as seal 3f in FIGS. 1 and 2. The bags and tubing are essentially transparent.

FIG. 1 shows one example of our system (a "closed" triple multiple blood bag system) used in conjunction with electronic fluid monitoring means. The main difference between the system of FIG. 1 and that of co-pending patent application Ser. No. 07/493,024 is in the middle bag, shown in more detail in FIGS. 2 and 3.

FIG. 2 shows the main bag 3 (the center bag) of FIG. 1 in more detail. As can be seen in FIG. 2, the bag 3 has a generally conventional appearance except for a longitudinal seal line 3f which extends from the top of the bag (and between at least 2 ports, 17a and 27a) downwardly to a position in the lower half of the bag but not to the bag bottom. By not quite extending to the bottom of the bag, a passageway 3d remains between the bulk of the bag interior 3g and a "channel" 3e running along side and generally parallel to the left side of the bag. The only "closed" communication between the upper ports 17a and 27a on either side of the longitudinal seal 3f is passageway 3d. In preferred embodiments passageway 3d and the width of the channel 3e should be as small as possible but large enough to permit non-turbulent and unobstructed flow of the lower bag contents out via tubing 17 when pressure is applied to the bag (after centrifugation of the whole blood or other blood component).

FIG. 3 illustrates a cross sectional view taken through lines 2—2 of FIG. 2 and shows the relatively small size and volume of the channel 3e compared to the remaining bag volume 3g.

After collection of whole blood via conventional needle assembly 3c and phlebotomy tubing 3a into a donor bag 3 such as that shown in FIG. 1, the blood is centrifuged at relatively high centrifugal force to form upper plasma component 9, intermediate buffy coat component 13, and lower red cell component 11. The bag 3 is then placed in a simple, conventional pressure-separator device (blood bag expresser) consisting of a moving spring-loaded expresser plate and a fixed plate.

In one very preferred embodiment, the separation system includes two on-off tubing clamps, 19 and 31, one on tubing 17 and one on tubing 27, activated by a sensor such as a photocell shown generally as box 16. The lower RBCs pass through port 17 while the upper plasma passes through port 27. Other ports (not shown) may be added as needed to the donor bag in place or in addition to bag access port 15. Passage of the bag contents through the attached tubings may be controlled using conventional frangible valves 3h (see FIG. 2). An example (preferred) of one such frangible valve is described in detail in U.S. Pat. No. 4,586,928 to B. Barnes et al.

At the start of the plasma expression, the valve 3h communicating with tubing 27 is open and the corresponding valve 3h for tubing 17 is closed. Plasma is expressed into bag 35 by pressure on bag 3 until red cells (in the buffy coat 13) are first seen or detected in tubing 27 by a photocell sensor positioned on the tubing 16, at which time clamp 31 on tubing 27 closes in response to an electrical signal on wire line 25 from the sensor and the clamp 19 on tubing 17 opens in response to a signal on similar line 25. Red cells are then expressed via passage way 3d through the top of bag 3 into, for example, a second satellite bag 21 containing a conventional red cell preservation solution such as AS-3 or the like (not shown). The expression continues until only a volume of about 50 to 60 ml (the buffy coat 13) remains in bag 3. This volume may be set, if desired, by a simple stop (not shown) between the expresser plate and the back plate against which the bag 3 is pressed in an otherwise conventional blood bag expresser. Optical sensors may be positioned at convenient places along lines 27 or 17 as needed to activate valves 31 and 19.

EXAMPLE

For test purposes, whole blood was collected into a bag containing a conventional anticoagulant and or preservative solution (CP2D/AS-3), then transferred into the "channel bag" of this disclosure. See bag 3 of FIG. 1. In practical use, however, the whole blood would be collected directly into the donor bag 3 via phlebotomy needle assembly 3a.

The blood unit was then centrifuged at about 3000Xg (2977Xg) for 9 minutes. Using a manual plasma expressor the upper plasma was expressed via tubing 17 into an empty bag 35. Red cells were then expressed through passageway 3d (see FIG. 2) and the "channel" (see 3e of FIG. 2) into additive bag 21. Expression of plasma was stopped when red cell layer was about 1 cm from the top of the bag. Expression of red cells was stopped when the pressure plate of plasma expressor reached a predetermined mark. At this point about 60 g of buffy coat (BC) remained in primary bag 3. About 60 g of plasma from bag 35 was expressed back to the BC in bag 3.

The BC in bag 3 was incubated overnight on a platelet agitator (to break up platelet aggregates) at about 22° C. The next morning the BC was transferred into another separation bag. An elongated separating bag as shown in U.S. Pat. No. 4,892,537 to R. Carmen et al for neocyte separations was used. This bag can be connected directly via tubing to an added port at the top of bag 3 for a truly closed system. The reconstituted BC (about 60 g BC in 60 g plasma) was centrifuged at 454Xg for 7 minutes. The top layer of platelet concentrate was then expressed into an attached TOTM plasticized PVC blood bag (see U.S. Pat. No. 4,280,497 to Warner et al) for storage study.

Platelet counts were performed on all fractions using either an electronic cell counter (plasma and platelet concentrate) or a manual method. Data are summarized in the table below.

TABLE

| | Platelets from Buffy Coat Data on Channel Bag (n = 9) | | |
|---|---|---|---|
| Fraction | Platelets No. × $10^{10}$ | Platelets % of Whole Blood | Leukocytes No. × $10^8$ |
| Whole blood | 13.6 ± 4.2 | 100 | |
| Plasma | 1.4 ± 0.6 | 10.3 | |
| Red Cells | 0.3 ± 0.4 | 2.2 | 12.4 ± 7.7 |
| Platelet Concentrate | 8.1 ± 2.4 | 59.5 | 0.2 ± 0.2 |
| Residual Buffy Coat | 3.0 ± 1.2 | 22.1 | |

The main bag of this disclosure provides manufacturing advantages since it can be made using conventional blood bag manufacturing methods. For example, many conventional blood bags are made by simply sealing the edges (perimeter) of two sheets of plasticized PVC film. The seal can be accomplished using conventional heat or radio frequency (RF) plastic sealing devices. Chemical solvent sealing, though possible, is less preferred because of possible seal failure or breakage.

The longitudinal seal for the preferred bag of this disclosure was made using an RF sealing device and this method of sealing is preferred for bags made from plasticized PVC. Bags made from other plastics (e.g., polyolefins) could be sealed, for example, using a simple heat seal.

We are unaware of the use of longitudinal seals in any blood bag system which are made to facilitate removal of the lower contents of a blood bag through the top of the bag. In U.S. Pat. No. 4,619,650 to L. Wisdom, however, a blood bag with a different type of longitudinal seal is shown. Although the central longitudinal seal of that bag appears to leave a passageway between two halves of the bag at the top (not the bottom) that bag would not allow the lower contents of the bag to be removed from the top of the bag as in the present system. More over, the purpose of the seal in that bag is to provide a line along which the bag can be torn open for the efficient removal (via machine) of frozen plasma.

Although the plasma bags of that patent do not disclose or suggest the present invention, the various ways to make blood bags taught in that patent and the blood bag patents cited above are incorporated into this disclosure by reference to those patents.

The main bag of this disclosure may be used for a gross separation of whole blood into plasma (PRP) and RBCs or, preferably, a finer separation of a blood component (e.g., the separation of platelets from the buffy coat portion of blood) as described above.

The sequence of component removal may be varied to suit a particular need or the availability (or non-availability) of expressors (machines designed to press a bag to squeeze out a given component).

For example, in our platelet preparation steps using the main bag of this disclosure, we now prefer to express the less dense plasma portion from the top of the bag first (before the RBCs are expressed). This is done to reduce the chance of inadvertently getting some of the platelets (in the buffy coat) into the channel from where it would be difficult to recover those platelets. By thus expressing the upper plasma (platelet poor plasma) first, the adjoining buffy coat is kept as far away from the channel entrance (passageway) as possible.

Thus, in our preferred method, we first express the plasma from the main bag. This leaves only the upper buffy coat and the lower RBCs in the bag. It should be understood that the upper buffy coat will contain some residual RBCs but, in general, there is a clearly visible interface between the buffy coat portion and the lower RBCs.

Since the volume of buffy coat portion in a typical unit of blood is about 50–60 ml, and since this amount is typically reconstituted with an equal amount of plasma (60 ml), this total volume (120 ml or about 120 g) can be used to determine how much of the RBCs should be expressed to leave behind only the buffy coat portion. For example, we have found that when a conventional blood bag expressor is used (either a V-expressor or a two-parallel plate expressor) the expressor can be marked to show a distance that the expressor plates should be apart to result in a remaining volume of about 120 ml (or about 120 g). After the position of the mark (can be a simple pencil mark) is set with about 120 ml of a fluid (e.g., water) the mark can then be used as a guide for future expressions of the red blood cells.

In a preferred method for preparing platelets from whole blood, a 50—50 mixture of buffy coat and plasma is made by transferring about 60 ml (or about 60 g) of plasma from the plasma collection bag back to the main bag. This mixture is then incubated overnight at room temperature with gentle agitation to break up platelet aggregates. Incubation can be in the original main bag (with the longitudinal seal) or in another bag to which it is expressed, preferably under closed conditions. Ideally any such other bag is preconnected via tubing to the main valve and includes an externally manipulated valve to control timing of the transfer.

We have found that the elongated bag of U.S. Pat. No. 4,892,537 to R. A. Carmen et al provides especially good platelet from buffy coat separations. That bag has a length to width ration of at least 2 to 1 and a tapering and portion that expands to form a funnel-like guide for directing a separated component from the bag after centrifugation.

In our application, the less dense platelets form the top portion after centrifugation of the buffy coat in the elongated bag. Those platelets are then expressed out for storage into yet another preconnected bag, preferably a bag suitable for such storage (e.g., a polyolefin bag or a plasticized PVC bag, either having been made from plastic having a relatively high gas transmissivity, helpful for platelet storage).

One such PVC bag is the TOTM plasticized bag of U.S. Pat. No. 4,280,497 to W. Warner et al. The bag described in that patent had wall thicknesses in the range of about 0.01 to 0.20. The walls had a $CO_2$ transmission of at last about 4000 ml/meter$^2$/day and an $O^2$ transmission of at least about 600 ml/meter$^2$/day. These rates would be considered relatively high gas transmissivity as the expression is used here.

Given the above disclosure it is thought variations will now occur to those skilled in the art. Accordingly, the above examples should be construed as illustrative and the scope of the invention disclosed herein should be limited only by the following claims.

We claim:

1. A method of separating a blood product into useful components comprising the sequential steps of
   (a) introducing the blood product into a blood bag having at least two ports at the top of the bag and a longitudinal seal extending downwardly from the top of the bag and between the two ports to at least the lower half of the bag, wherien a channel is formed on one side of the longitudinal seal;
   (b) centrifuging the blood to separate the blood into an upper less dense portion and a lower more dense portion, and;
   (c) expressing the more dense portion out of the bag from the lower portion of the bag via the channel and a port with which the channel communicates.

2. The method of claim 1 wherein the blood product is whole blood, the less dense portion is plasma and the more dense portion is red blood cells.

3. The method of claim 1 wherien the expression of the red blood cells is monitored using electronic monitoring means.

4. A method of preparing platelets from whole blood comprising the sequential steps of
   (a) introducing whole blood into a blood bag having at least two ports at the top of the bag and a longitudinal seal extending downwardly for the top of the bag and between the ports to the lower half of the bag, wherein a channel is formed on one side of the longitudinal seal;
   (b) centrifuging the bag and its whole blood contents to form a lower more dense portion of red blood cells, an upper less dense portion of plasma and an intermediate buffy coat portion comprising platelets and while blood cells;
   (c) expressing the plasma portion out of the bag via one of the ports at the top of the bag and on one side of the longitudinal seal and expressing the red blood cell portion out of the bag via the channel on the other side of the longitudinal seal and a port with which the channel communicates;
   (d) then subjecting the remaining buffy coat portion to conditions sufficient to separate platelets from the buffy coat portion.

5. The method of claim 4 wherein the buffy coat portion of step (d) is expressed from the bag into another bag connected via tubing to the top of the bag having the longitudinal seal.

6. The method of claim 5 wherein the other bag is elongated, having a length to width ratio of at least 2 to 1 and adapted to facilitate separation of platelets from the buffy coat portion when the elongated bag containing the buffy coat portion is centrifuged under conditions sufficient to encourage separation of the platelets from the buffy coat portion.

7. The method of claim 6 wherein the elongated bag has attached thereto via tubing yet another bag suitable for storage of platelets.

8. The method of claim 7 wherein the bag suitable for storage of platelets.

9. The method of claim 8 wherein the bag suitable for storage of platelets comprises a bag made from a plastic film having a relatively high gas transmissivity.

10. The method of claim 8 wherein the bag suitable for storage of platelets includes a platelet storage solution.

* * * * *